US012745978B2

(12) United States Patent
Joo et al.

(10) Patent No.: US 12,745,978 B2
(45) Date of Patent: Sep. 29, 2026

(54) DEVICE FOR MEASURING OBSTRUCTION OF TRACHEOSTOMY TUBE, TRACHEA, AND BRONCHUS OF PATIENT WITH TRACHEOSTOMY TUBE

(71) Applicants: THE CATHOLIC UNIVERSITY OF KOREA INDUSTRY-ACADEMIC COOPERATION FOUNDATION, Seoul (KR); INDUSTRY-ACADEMIC COOPERATION FOUNDATION, YONSEI UNIVERSITY, Seoul (KR)

(72) Inventors: Young Hoon Joo, Seoul (KR); Hyun Bum Kim, Seoul (KR); Jong Baeg Kim, Seoul (KR); Yo Han Jung, Seoul (KR); Dae Yeon Koh, Seoul (KR); Min Hyeong Kim, Seoul (KR); Hyun Jun Han, Seoul (KR)

(73) Assignees: THE CATHOLIC UNIVERSITY OF KOREA INDUSTRY-ACADEMIC COOPERATION FOUNDATION, Seoul (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 79 days.

(21) Appl. No.: 18/838,718

(22) PCT Filed: Aug. 12, 2022

(86) PCT No.: PCT/KR2022/012099

§ 371 (c)(1),
(2) Date: Aug. 15, 2024

(87) PCT Pub. No.: WO2023/243764

PCT Pub. Date: Dec. 21, 2023

(65) Prior Publication Data

US 2025/0169791 A1 May 29, 2025

(30) Foreign Application Priority Data

Jun. 16, 2022 (KR) ........................ 10-2022-0073207

(51) Int. Cl.
*A61B 8/08* (2006.01)
*A61B 8/00* (2006.01)

(52) U.S. Cl.
CPC ............ *A61B 8/0833* (2013.01); *A61B 8/461* (2013.01); *A61B 8/5223* (2013.01); *A61B 8/565* (2013.01)

(58) Field of Classification Search
CPC ..... A61B 8/0833; A61B 8/461; A61B 8/5223; A61B 8/565; A61B 8/085
See application file for complete search history.

(56) References Cited

U.S. PATENT DOCUMENTS 5,445,144 A * 8/1995 Wodicka ............ A61M 16/202 128/207.14
2019/0247050 A1 * 8/2019 Goldsmith ................ A61F 2/82

FOREIGN PATENT DOCUMENTS

JP 2005-168883 A 6/2005
JP 2012-517303 A 8/2012
(Continued)

*Primary Examiner* — Bo Joseph Peng
(74) *Attorney, Agent, or Firm* — Bridgeway IP Law Group, PLLC; Jihun Kim

(57) ABSTRACT

An embodiment provides a device for measuring the obstruction of a tracheostomy tube, the trachea, and the bronchus, the device comprising an obstruction measurement unit (100) which is coupled to the entrance (11) of a tracheostomy tube where tracheostomy has been performed, and transmits a sound wave and receives a reflected sound wave to measure an obstruction site in any one of the tracheostomy tube (A), the trachea (B), and the bronchus (C).

13 Claims, 6 Drawing Sheets

(56) References Cited

FOREIGN PATENT DOCUMENTS

| | | | |
|---|---|---|---|
| JP | 2014-057688 | A | 4/2014 |
| KR | 10-2314270 | B1 | 10/2021 |
| WO | 93-11703 | A1 | 6/1993 |
| WO | 2020-118138 | A1 | 6/2020 |

* cited by examiner

300

300

DEVICE FOR MEASURING OBSTRUCTION OF TRACHEOSTOMY TUBE, TRACHEA, AND BRONCHUS OF PATIENT WITH TRACHEOSTOMY TUBE

TECHNICAL FIELD

The present invention relates to a device for measuring the obstruction of the tracheostomy tube, trachea, and bronchus of a tracheostomy tube patient, and more specifically, to a device for measuring the obstruction of the tracheostomy tube, trachea, and bronchus, wherein it is possible to determine the degree of the obstruction of the tracheostomy tube, trachea, and bronchus by analyzing changes in volume according to sites in the tracheostomy tube, trachea, and bronchus of a tracheostomy tube patient using a sound wave.

BACKGROUND ART

As the population ages and chronic diseases increase, respiratory diseases such as stroke and aspiration pneumonia are increasing, and tracheostomy or tracheotomy is being performed as a treatment for these diseases.

Since tracheostomy is performed in the trachea, the middle part of the human airway, the humidification and dust removal functions of the upper airway are insufficient, and thus more sputum is produced than usual; if the sputum is not properly removed, stenosis and occlusion of the tracheostomy tube may occur, resulting in secondary respiratory failure or dyspnea. If occlusion occurs and is not resolved within 10 minutes, it may lead to death.

Appropriate sputum removal is performed directly by a patient or by an outsider such as a nurse, caregiver, or guardian; for patients who are unconscious or have difficulty communicating, sputum removal is performed entirely by an outsider 24 hours a day. Since the timing of sputum removal varies from person to person depending on the environment and weather, regular suctioning is performed at 1 to 2 hour intervals, or an outsider listens to the breathing sound, determines the degree of obstruction, and performs suctioning.

Problems may occur when sputum removal is insufficient, and too frequent and random suctioning may also cause severe coughing, which may damage the tracheal wall or cause breathing difficulties or put a lot of strain on the heart.

RELATED ART DOCUMENT

Republic of Korea Patent No. 10-2314270

DETAILED DESCRIPTION OF THE INVENTION

Technical Problem

To this end, the present invention is to provide a device for measuring the obstruction of the tracheostomy tube, trachea, and bronchus of a tracheostomy tube patient, wherein it is possible to determine the degree of the obstruction of the tracheostomy tube, trachea, and bronchus by analyzing changes in volume according to sites in the tracheostomy tube, trachea, and bronchus using a sound wave.

The aspect of the present invention is not limited to that mentioned above, and other aspects not mentioned will be clearly understood by those skilled in the art from the description below.

Technical Solution

An embodiment of the present invention provides a device for measuring the obstruction of the tracheostomy tube, the trachea, and the bronchus, the device including an obstruction measurement unit 100 which is coupled to a tracheostomy tube entrance 11 where tracheostomy has been performed, and transmits a sound wave and receives a reflected sound wave to measure an obstruction degree in any one of the tracheostomy tube A, the trachea B, and the bronchus C.

The obstruction measurement unit 100 may include: a sound source generation unit 101 that generates and outputs a sound source signal of the sound wave; a sound wave transmission unit 110 that receives the sound source signal, and generates and transmits a sound wave; a sound wave reception unit 120 that receives a reflected sound wave from the inside of any one of the tracheostomy tube A, trachea B, or bronchus C; and a sound wave analysis unit 130 that calculates a reflected site using the transmission and reception time of the received sound wave, and then calculates the internal cross-sectional area or volume of any one of the tracheostomy tube A, trachea B, or bronchus C to output the obstruction degree.

The obstruction degree may include an obstruction site 3 as distance information and cross-sectional area or volume information of the obstruction site 3.

The sound wave analysis unit 130 may further include a near field communication unit 131 that transmits an obstruction alarm when the internal cross-sectional area or volume of any one of the calculated tracheostomy tube A, trachea B or bronchus C is smaller than a preset cross-sectional area or volume.

The device for measuring the obstruction of the tracheostomy tube, the trachea, and the bronchus may further include a body connection unit 33 in which in order to identify the starting point of an internal obstruction site of any one of the tracheostomy tube A, trachea B or bronchus C, a distance reference unit 34 forming a preset cross-sectional area or volume area is formed inside a sound wave route to connect the connection tube 31 to the tracheostomy tube entrance 11.

The device for measuring the obstruction of the tracheostomy tube, the trachea, and the bronchus may further include a display unit 300 that indicates an obstruction site of one of the tracheostomy tube A, trachea B, or bronchus C measured in the obstruction measurement unit 100.

The display unit 300 may further include an obstruction notification unit 310 that outputs an obstruction alarm when the calculated internal cross-sectional area or volume of any one of the tracheostomy tube A, trachea B, or bronchus C is smaller than a preset cross-sectional area or volume.

The sound wave may include at least one of a low frequency sound wave, an audible frequency sound wave or an ultrasonic wave.

Another embodiment of the present invention provides a device for measuring the obstruction of the tracheostomy tube, the trachea, and the bronchus, the device including: a body 30 having an obstruction measurement unit 100 built therein; a body connection unit 33 connected to a tracheostomy tube entrance 11; a connection tube 31 connecting the body 30 and the body connection unit 33; and a display unit 300 connected to the body 30 and outputting at least one of an operating status of the body 30, obstruction measurement information, and an obstruction alarm.

The obstruction measurement unit 10 may include: a sound source generation unit 101 that generates a sound source signal of a sound wave; a sound wave transmission unit 110 that generates and transmits a sound wave using the sound source signal; a sound wave reception unit 120 that receives a reflected sound wave from the inside of one of the tracheostomy tube A, trachea B, or bronchus C; and a sound wave analysis unit 130 that calculates the reflected site using the transmission and reception time of the received sound wave, and then calculates the internal cross-sectional area or volume of one of the tracheostomy tube A, trachea B, or bronchus C to output an obstruction degree.

The obstruction measurement unit 100 may further include a near field communication unit 131 that performs communication with external devices.

As described above, the sound wave may include at least one of a low frequency sound wave, an audible frequency sound wave or an ultrasonic wave.

The connection tube 31 may be configured as a flexible tube that guides a sound wave from the sound wave transmission unit 110 of the body 30 to the body connection unit 33 and guides a sound wave from the tracheostomy tube A, trachea B, or bronchus C to the sound wave reception unit 120.

The body connection unit 33 may further include a distance reference unit 34 having a preset cross-sectional area or volume.

The device for measuring the obstruction of the tracheostomy tube, the trachea, and the bronchus may further include a replacement coupling tube 35 that replaceably connects the body connection unit 33 and the tracheostomy tube entrance 11.

The replacement coupling tube 35 may further include a distance start display unit 36 that provides a distance indication reference site of the display unit 300 by having a preset cross-section or volume in a sound wave flow path inside.

ADVANTAGEOUS EFFECTS

An embodiment of the present invention described above provides an effect of significantly facilitating sputum suction by accurately detecting the degree of obstruction and the site of obstruction due to sputum in one of the tracheostomy tube A, trachea B, or bronchus C of a tracheostomy patient.

In addition, an embodiment of the present invention provides an effect of rapidly removing obstruction by accurately detecting the degree of obstruction and the site of obstruction due to sputum in one of the tracheostomy tube A, trachea B, or bronchus C of a tracheostomy patient.

This also provides an effect of solving the conventional problem of tracheal wall damage and violent coughing caused by frequent aspiration performed without knowing the presence or amount of sputum.

The effects of the present invention are not limited to the effects described above, and should be understood to include all effects that are inferable from the configuration of the present invention described in the detailed description or claims of the present invention.

MODE FOR CARRYING OUT THE INVENTION

Figure 1:
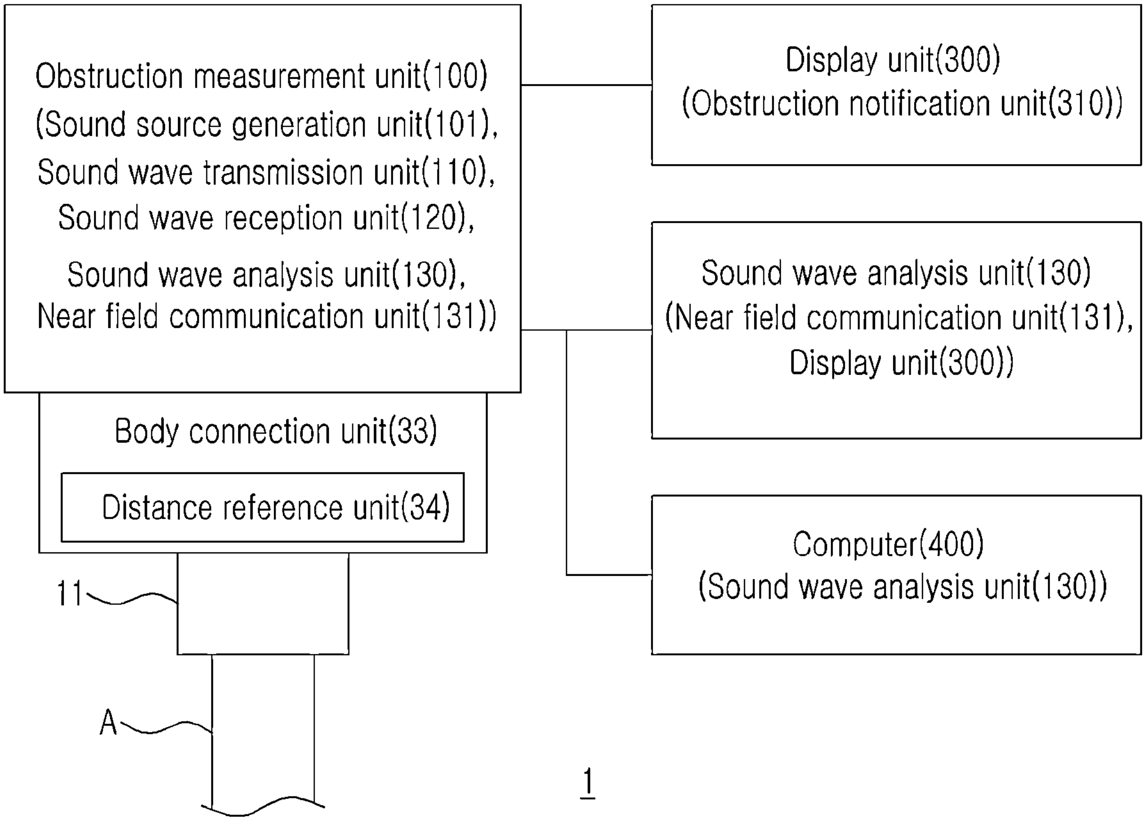
FIG. 1 is a functional block diagram of a device for measuring the obstruction of the tracheostomy tube, the trachea, and the bronchus of an embodiment of the present invention.

In the following description of the present invention, if it is determined that a specific description of a related known function or configuration may unnecessarily obscure the gist of the present invention, the detailed description will be omitted.

Since the embodiments according to the concept of the present invention may have various changes and may have various forms, specific embodiments are illustrated in the drawings and described in detail in this specification or application. However, this is not intended to limit the embodiments according to the concept of the present invention to a specific disclosure form, and it should be understood that the present invention includes all changes, equivalents, and substitutes included in the spirit and technical scope of the present invention.

When it is said that a component is “connected” or “contacted” to another component, it should be understood that the component may be directly connected to or in contact with the other component, but that there may be another component in between. On the other hand, when it is said that a component is “directly connected” or “directly in contact with” to another component, it should be understood that there is no other component in between. Other expressions that describe the relationship between components, such as “between” and “directly between” or “adjacent to” and “directly adjacent to”, should be interpreted similarly.

The terminology used in this specification is used only to describe specific embodiments and is not intended to limit the present invention. The singular expression includes the plural expression unless the context clearly indicates otherwise. In this specification, the terms “include” or “have” should be understood to indicate the presence of a described feature, number, step, operation, component, part, or combination thereof, but do not preclude the possibility of the presence or addition of one or more other features, numbers, steps, operations, components, parts, or combinations thereof.

Hereinafter, the present invention will be described in more detail with reference to the accompanying drawings showing embodiments of the present invention.

Figure 2:
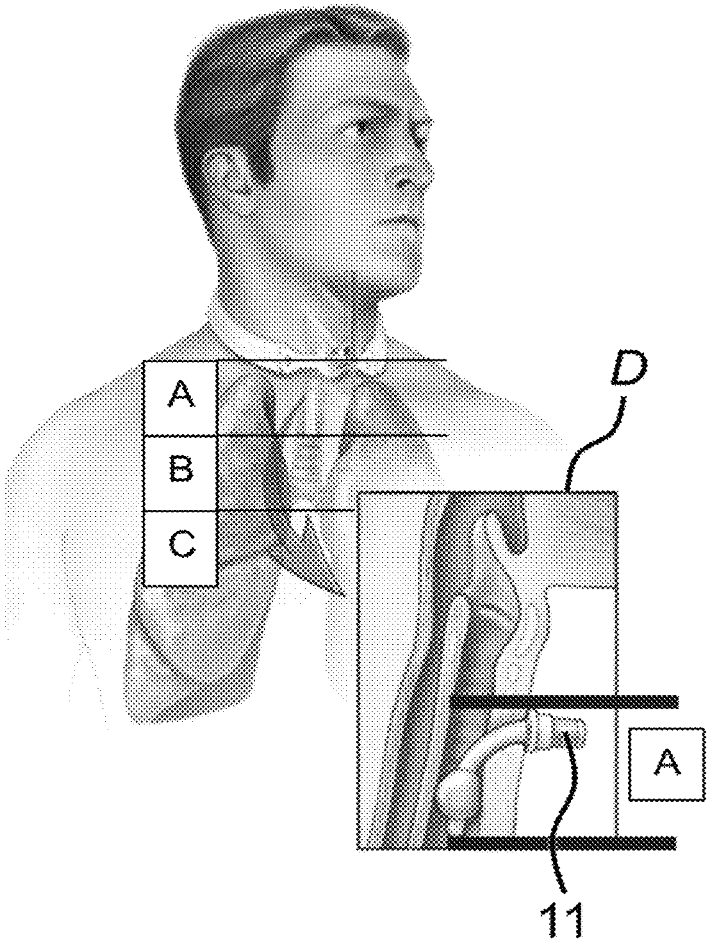
FIG. 2 is a view showing the tracheostomy tube A, the trachea B, the bronchus C, and an enlarged view D of a tracheostomy tube A area of a patient who underwent tracheostomy.

FIG. 1 is a functional block diagram of a device for measuring the obstruction of the tracheostomy tube, the trachea, and the bronchus of an embodiment of the present invention, and FIG. 2 is a view showing the tracheostomy tube A, the trachea B, the bronchus C, and an enlarged view D of a tracheostomy tube A area of a patient who underwent tracheostomy.

As in FIGS. 1 and 2, a device 1 for measuring the obstruction of the tracheostomy tube, the trachea, and the bronchus may include an obstruction measurement unit 100 which is coupled to a tracheostomy tube entrance 11 where tracheostomy has been performed, and transmits a sound wave and receives a reflected sound wave to measure an obstruction degree in any one of the tracheostomy tube A, the trachea B, and the bronchus C.

The device 1 for measuring the obstruction of the tracheostomy tube, the trachea, and the bronchus may include a display unit 300 that indicates an obstruction site of one of the tracheostomy tube A, trachea B, or bronchus C measured in the obstruction measurement unit 100.

As in FIG. 2, the tracheostomy tube A is inserted and fixed into the lower part of the upper airway in a patient who has undergone tracheostomy. In addition, the lower part of the tracheostomy tube A is maintained by the trachea B as is, and the bronchus C is located at the lower part of the trachea B to be connected to the lungs.

The tracheostomy tube A includes a tracheostomy tube entrance 11. Since having to be able to be connected to a ventilator, the tracheostomy tube entrance 11 has a shape and size that are consistent regardless of the manufacturer and tube size.

The obstruction measurement unit 100 may be configured to measure whether there is the obstruction by receiving a sound wave reflected from the inner wall of one of the tracheostomy tube A, the trachea B, or the bronchus C and calculating the cross-sectional area or volume of the inside of one of the tracheostomy tube A, the trachea B, or the bronchus C.

To this end, the obstruction measurement unit 100 may include: a sound source generation unit 101 that generates and outputs a sound source signal of the sound wave; a sound wave transmission unit 110 that receives the sound source signal, and generates and transmits a sound wave; a sound wave reception unit 120 that receives a reflected sound wave from the inside of any one of the tracheostomy tube A, trachea B, or bronchus C; and a sound wave analysis unit 130 that calculates a reflected site using the transmission and reception time of the received sound wave, and then calculates the internal cross-sectional area or volume of any one of the tracheostomy tube A, trachea B, or bronchus C to output the obstruction degree.

The sound wave analysis unit 130 may further include a near field communication unit 131 that transmits an obstruction alarm when the internal cross-sectional area or volume of any one of the calculated tracheostomy tube A, trachea B or bronchus C is smaller than a preset cross-sectional area or volume.

In addition, the device 1 for measuring the obstruction of the tracheostomy tube, the trachea, and the bronchus may further include a body connection unit 33 that connects the obstruction measurement unit 100 to the tracheostomy tube entrance 11.

Figure 6:
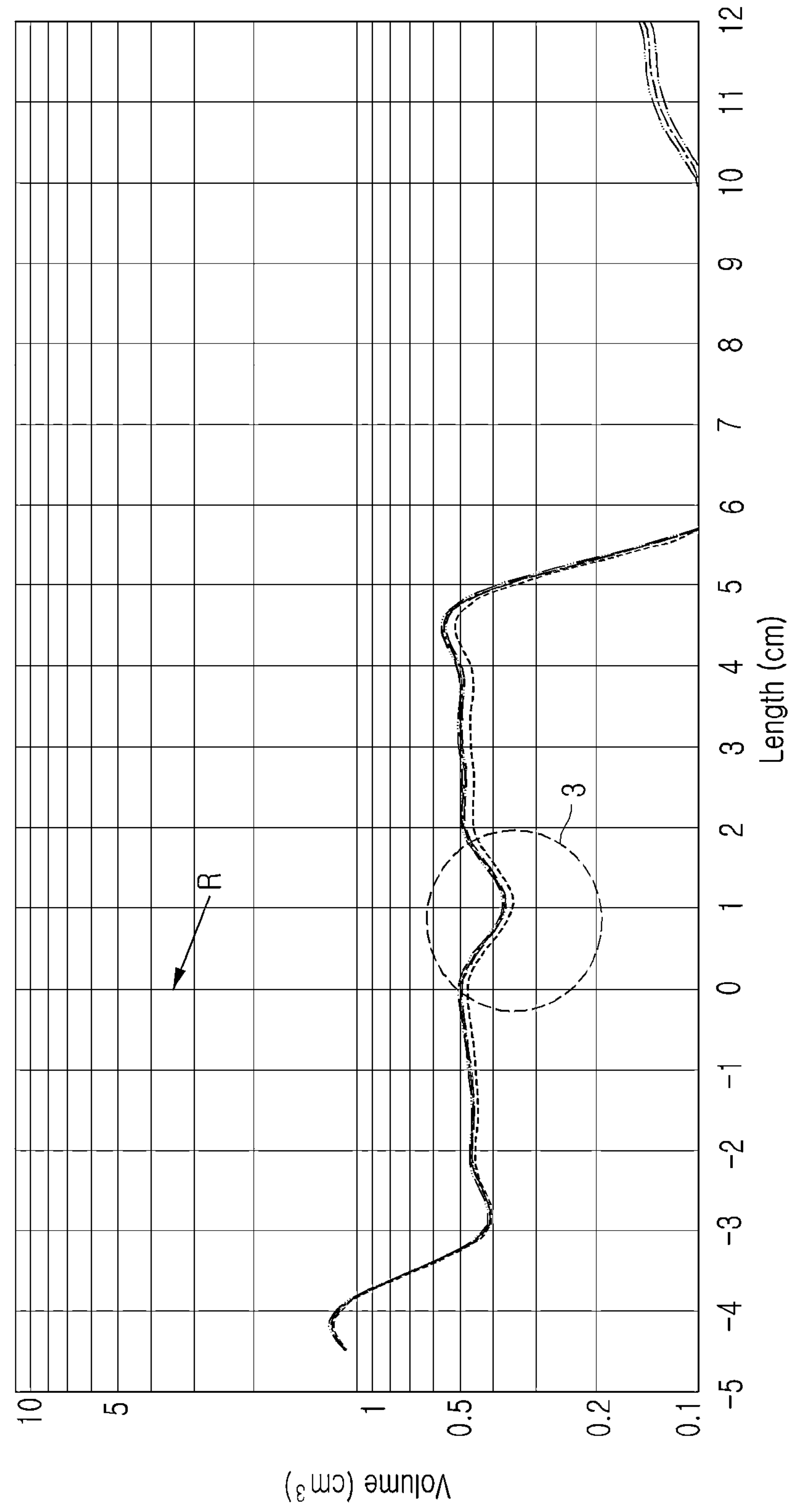
FIG. 6 is a view of a display unit 300 that displays a graph of changes in the cross-sectional area or volume measured according to sites in the tracheostomy tube A in an obstructed state and an obstruction site 3 indicated.

In addition, the body connection unit 33 may further include a distance reference unit 34 forming a preset cross-sectional area or volume in a specific site on an inner tube path in which a sound wave is guided, in order to identify the starting point of an obstruction site 3 (see FIG. 6).

The distance reference unit 34 enables the sound wave analysis unit 130 to measure the distance based on the distance reference unit 34 even if the length of the connection tube 31 (see FIG. 3) connecting the sound wave transmission unit 110 and the tracheostomy tube entrance 11 is not fixed.

The body connection unit 33 is configured to be connected to the tracheostomy tube entrance 11. Since the tracheostomy tube entrance 11 is always manufactured to a standard specification, the body connection unit 33 may be manufactured so as to be connected to a tracheostomy tube A of any specification.

The display unit 300 may further include an obstruction notification unit 310 that outputs an obstruction alarm when the calculated internal cross-sectional area or volume of any one of the tracheostomy tube A, trachea B, or bronchus C is smaller than a preset cross-sectional area or volume. At this time, since it is not possible to remove phlegm in the bronchus C without a bronchus endoscope, the obstruction measurement unit 100 may be configured to display the site where the volume doubles as the site of the bronchus C.

The obstruction notification unit 310 may include a speaker that outputs an obstruction alarm sound or a lamp that outputs a progress signal. The progress signal may be displayed by the flashing of the display unit.

The sound wave applied to the device 1 for measuring the obstruction of the tracheostomy tube, the trachea, and the bronchus of an embodiment of the present invention may include at least one of a low-frequency sound wave, an audible frequency sound wave, or an ultrasonic wave.

The device 1 for measuring the obstruction of the tracheostomy tube, the trachea, and the bronchus of an embodiment of the present invention, which has the above-described configuration, may be manufactured to be portable, including a monitor, including a display unit 300.

In addition, the device may be configured to be able to be connected to a computer. In this case, like a computer 400 indicated by the dotted line in FIG. 1, the sound wave analysis unit 130 may be configured to be independently configured as software or hardware and installed on the computer 400.

In the case of being portable, if a value is less than a preset value, the device may be configured to transmit only the degree of obstruction or non-obstruction through a microphone in the display unit or the near field communication unit 131 such as a Bluetooth infrared communication unit. If a device is manufactured as portable, measurement is often performed by non-medical personnel, and thus the expression and display should be easily expressed. For example, even when a graph is shown, a normal green range and an abnormal red area may be expressed. In addition, if a device is manufactured as portable, it is desirable to manufacture the device so that charging and usage are easy.

Figure 3:
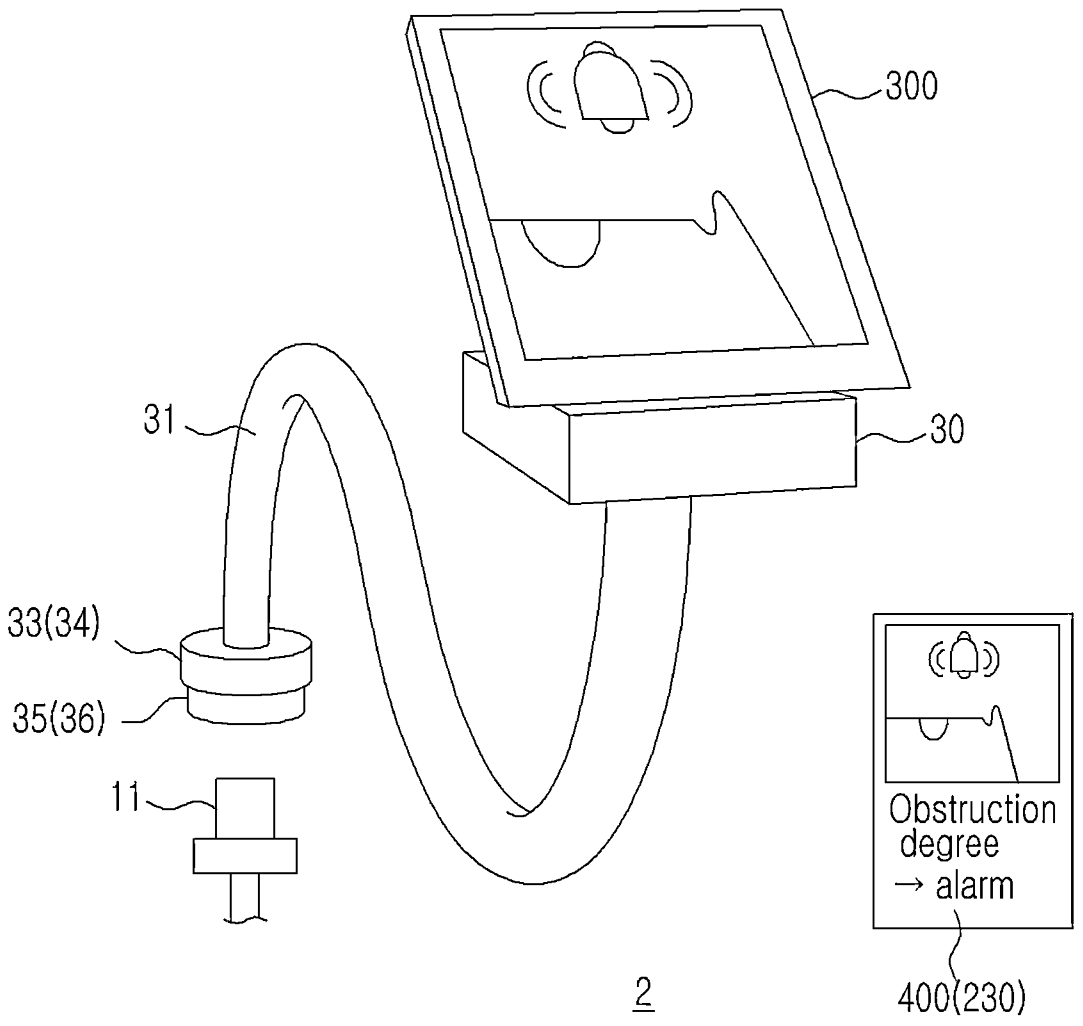
FIG. 3 is a perspective view of a device 2 for measuring the obstruction of the tracheostomy tube, the trachea, and the bronchus of an embodiment of the present invention.
Figure 4:
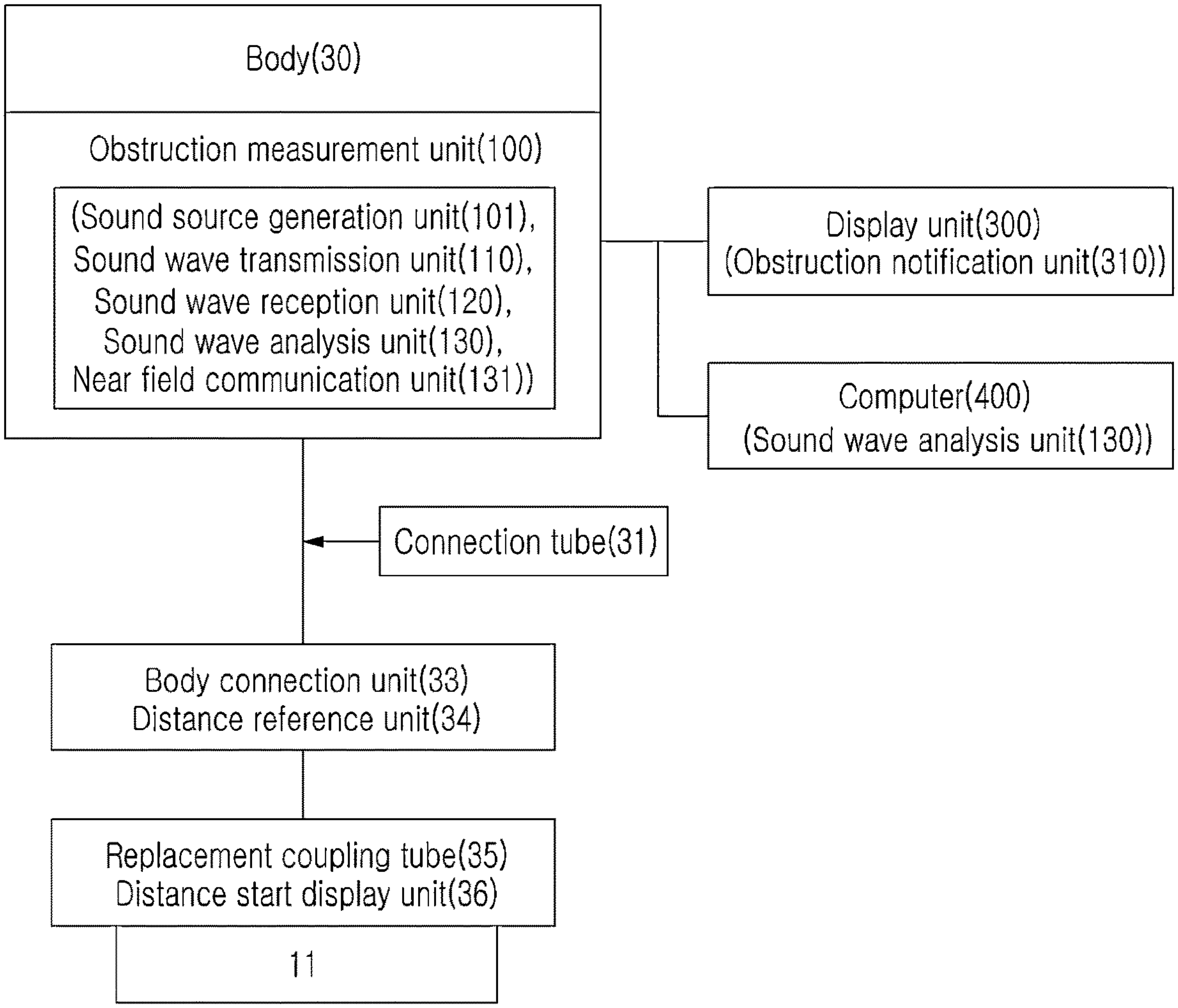
FIG. 4 is a functional block diagram of the device 2 for measuring the obstruction of the tracheostomy tube, the trachea, and the bronchus of FIG. 3.

FIG. 3 is a perspective view of a device 2 for measuring the obstruction of the tracheostomy tube, the trachea, and the bronchus of an embodiment of the present invention, and FIG. 4 is a functional block diagram of the device 2 for measuring the obstruction of the tracheostomy tube, the trachea, and the bronchus of FIG. 3.

As in FIGS. 3 and 4, a device 2 for measuring the obstruction of the tracheostomy tube, the trachea, and the bronchus of the present invention may include: a body 30 having an obstruction measurement unit 100 built therein; a body connection unit 33 connected to a tracheostomy tube entrance 11; a connection tube 31 connecting the body 30 and the body connection unit 33; and a display unit 300 connected to the body 30 and outputting at least one of an operating status of the body 30, obstruction measurement information, and an obstruction alarm.

As in FIG. 4, the obstruction measurement unit 10 may include: a sound source generation unit 101 that generates a sound source signal of a sound wave; a sound wave transmission unit 110 that generates and transmits a sound wave using the sound source signal; a sound wave reception unit 120 that receives a reflected sound wave from the inside of one of the tracheostomy tube A, trachea B, or bronchus C;

and a sound wave analysis unit 130 that calculates the reflected site using the transmission and reception time of the received sound wave, and then calculates the internal cross-sectional area or volume of one of the tracheostomy tube A, trachea B, or bronchus C to output an obstruction degree.

In addition, the obstruction measurement unit 100 may further include a near field communication unit 131 that performs communication with external devices.

The sound source generation unit 101 may be configured to generate and supply a sound source signal of the sound wave to the obstruction measurement unit 100. At this time, the sound wave may include at least one of a low frequency sound wave, an audible frequency sound wave, or an ultrasonic wave, as described above.

The sound wave transmission unit 110 may be configured as a transmitter that receives the sound source signal, generates a sound wave, and transmits the sound wave.

The above connection tube 31 may be configured to connect a sound wave from the sound wave transmission unit 110 of the body 30 to the body connection unit 33 and connects a sound wave from the tracheostomy tube A, trachea B, or bronchus C to the sound wave reception unit 120, and to allow distance adjustment as a flexible tube.

The body connection unit 33 is a part that is coupled to the tracheostomy tube entrance 11 where the tracheostomy is performed, and acts as a passage through which a sound wave from the sound wave transmission unit 110 may travel to the tracheostomy tube A, trachea B, or bronchus C.

The body connection unit 33, which is configured to connect the body 30 to the tracheostomy tube entrance 11, serves to prevent a sound wave from leaking out and is closed except when transmitting sound waves, so as to prevent contamination that occurs during normal or measurement times, thereby preventing problems that may arise in terms of hygiene.

The body connection unit 33 may further include a distance reference unit 34 forming a preset cross-sectional area or volume in a specific site on an inner tube path in which a sound wave is guided, in order to identify the starting point of an obstruction site 3 (see FIG. 6).

The distance reference unit 34 enables the sound wave analysis unit 130 to measure the distance based on the distance reference unit 34 even if the length of the connection tube 31 (see FIG. 3) connecting the sound wave transmission unit 110 and the tracheostomy tube entrance 11 is not fixed.

The body connection unit 33 is configured to be connected to the tracheostomy tube entrance 11. Since the tracheostomy tube entrance 11 is always manufactured to a standard specification, the body connection unit 33 may be manufactured so as to be connected to a tracheostomy tube A of any specification.

The device 2 for measuring the obstruction of the tracheostomy tube, the trachea, and the bronchus may further include a replacement coupling tube 35 that replaceably connects the body connection unit 33 and the tracheostomy tube entrance 11. The replacement coupling tube 35 may be configured to connect the body connection unit 33 and the tracheostomy tube entrance 11. When the device 2 for measuring the obstruction of the tracheostomy tube, the trachea, and the bronchus is used for multiple patients, the replacement coupling tube 35 may be replaced and applied to prevent the spread of infection that may occur due to usage for multiple patients, thereby improving hygiene.

The replacement coupling tube 35 may further include a distance start display unit 36 that is formed as a certain area having a preset cross-sectional area or volume different from the distance reference unit 34 at a specific site on an inner tube path in which a sound wave is guided, and is displayed as a distance start display site R (see FIG. 6) that serves as a distance measurement standard displayed on the display unit 300.

When the replacement coupling tube 35 is coupled to the body connection unit 33, the distance reference unit 34 and the distance start display unit 36 may be formed to always have a constant value distance.

The sound wave analysis unit 130 described below uses the distance start display unit 36 as a reference point for distance measurement by detecting the preset cross-sectional area or volume when performing sound wave analysis. In addition, the sound wave analysis unit 130 measures the distance between the distance reference unit 34 and the distance start display unit 36 to check whether a constant value is always output, so that errors and mistakes are checked in advance. Therefore, even if the distance between the sound wave transmission unit 110 and the connection tube 31 is not fixed, the sound wave analysis unit 130 may measure the distance based on the distance reference unit 34 and the distance start display unit 36.

In addition, the replacement coupling tube 35 may be configured so that the distance start display site is engraved at the outside of a site corresponding to the distance start display unit 36. In this case, when performing suction using a tube with a graduated mark, this may be configured so that the end of the tube is easily positioned at the obstruction site 3 by functioning as a reference position for confirming the insertion length of the tube.

The body connection unit 33 and the replacement coupling tube 25 of the above-described configuration are configured to be connected to a patient's tracheostomy tube entrance 11. Since the tracheostomy tube entrance 11 is always manufactured to a standard specification, the body connection unit 33 and the replacement coupling tube 25 may be manufactured so as to be connected to a tracheostomy tube A of any specification.

In the device 2 for measuring the obstruction of the tracheostomy tube, the trachea, and the bronchus of the above-described configuration, the sound source generation unit 101 generates a sound source signal, and the sound wave transmission unit 110 generates and transmits a sound wave using the sound source signal. The sound wave reception unit 120 receives a reflected sound wave from an inner wall of any one of the tracheostomy tube A, trachea B, or bronchus C, and calculates the cross-sectional area or volume of the inside of any one of the tracheostomy tube A, trachea B, or bronchus C, thereby measuring whether there is obstruction.

The sound wave analysis unit 130 receives a reflected sound wave from the inside of any one of the tracheostomy tube A, trachea B, or bronchus C. The sound wave analysis unit 130 calculates a site where a sound wave is reflected from the distance reference unit 34 using the transmission and reception time of the received sound wave. In addition, the sound wave analysis unit 130 is configured to output an obstruction degree by calculating the internal cross-sectional area or volume of one of the tracheostomy tube A, trachea B, or bronchus C. The internal cross-sectional area or volume of any one of the tracheostomy tube A, trachea B, or bronchus C may be measured by analyzing the amplitude change of a transmitted sound wave and a reflected sound wave from the sound wave transmission unit 110.

The near field communication unit 131 may be configured to determine an obstruction site 3 (see FIG. 6) and transmit an obstruction alarm, if the data source received from the sound wave receiving unit 120 as a result of the sound wave analysis or the generated internal cross-sectional area or volume of any one of the tracheostomy tube A, trachea B, or bronchus C is smaller than the preset cross-sectional area or volume.

The display unit 300 may be configured to include an obstruction notification unit 310. Therefore, the display unit 300 may display an obstruction alarm along with a corresponding site in the case of the obstruction of one of the tracheostomy tube A, trachea B, or bronchus C.

The the device 2 for measuring the obstruction of the tracheostomy tube, the trachea, and the bronchus may transmit the contents analyzed by the sound wave analysis unit 130 to a nearby computer or a cloud 400 through the near field communication unit 131. In addition, the data received from the sound wave reception unit 120 as is may be connected to a nearby computer or a cloud 400 using the near field communication unit 131, and the sound wave analysis unit 130 built into the computer or cloud may analyze a sound wave and transmit information to the display unit 300 and the obstruction notification unit 410 through the near field communication unit 131.

An obstruction measurement process by the device 1, 2 for measuring the obstruction of the tracheostomy tube, the trachea, and the bronchus of an embodiment of the present invention having the above-described configurations is described.

After connecting the obstruction measurement unit 100 to the tracheostomy tube entrance 11 to measure obstruction, a sound wave is transmitted for about 1 to 2 seconds and then received to measure the cross-sectional area or volume according to sites from the tracheostomy tube A to the bronchus C, and then an obstruction degree is analyzed.

First, in the case of the tracheostomy tube A, there are slight differences depending on the company, but the tubes are supplied by size and the internal volume and length are constant. Therefore, the internal cross-sectional area or volume of the tracheostomy tube A should be constant and is predictable. Therefore, if the measured internal cross-sectional area or volume is smaller than a predicted value, it may be determined that this is the obstruction by sputum. In this case, the tracheostomy tube A or a tube of the tracheostomy tube A should be replaced.

Figure 5:
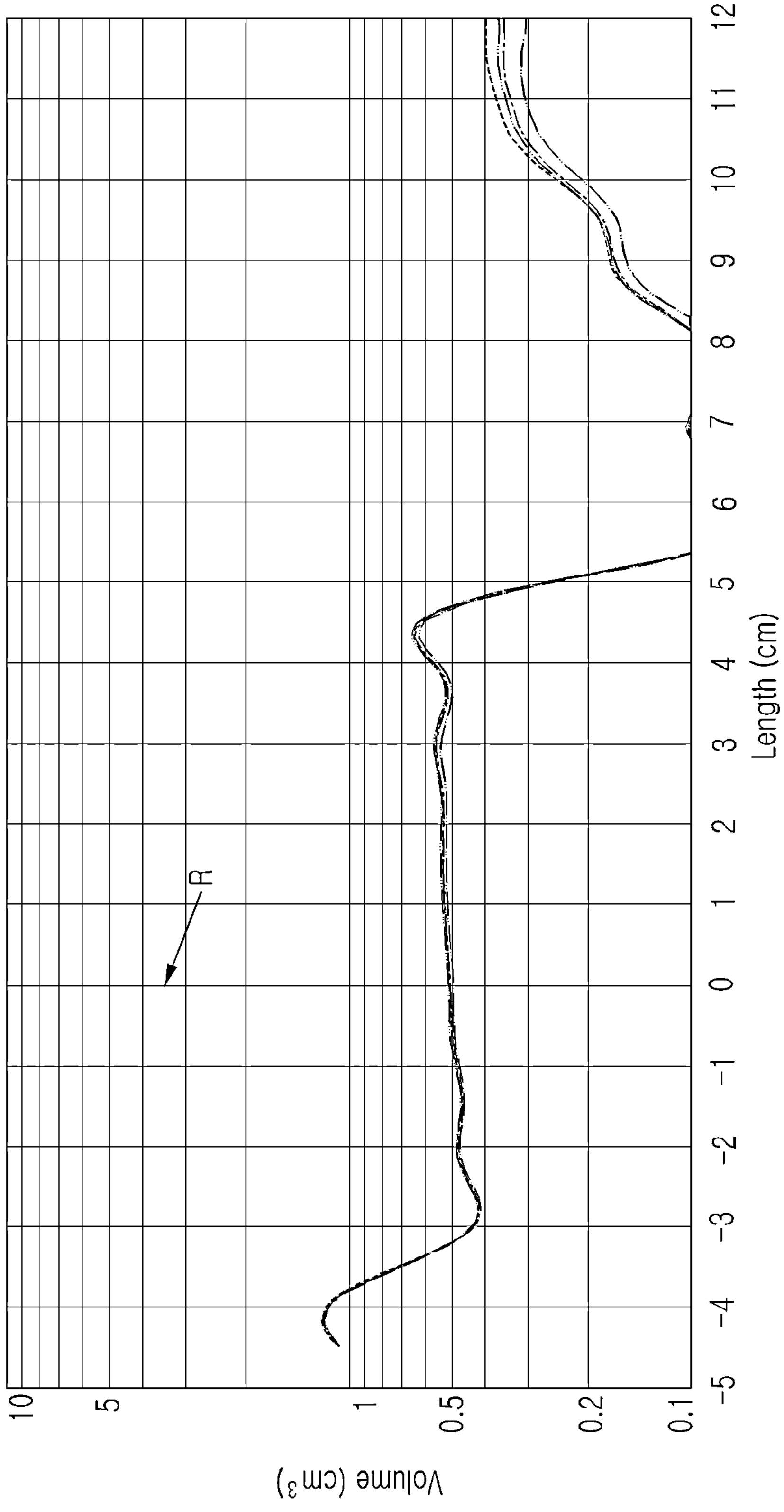
FIG. 5 is a view of a display unit 300 that displays a graph of changes in the cross-sectional area or volume measured according to sites in the tracheostomy tube A in an unobstructed state.

FIG. 5 is a view of a display unit 300 that displays a graph of changes in the cross-sectional area or volume measured according to sites in the tracheostomy tube A in an unobstructed state, and FIG. 6 is a view of a display unit 300 that displays a graph of changes in the cross-sectional area or volume measured according to sites in the tracheostomy tube A in an obstructed state and an obstruction site 3 indicated.

In FIG. 5 and FIG. 6, R represents a distance start display unit site R corresponding to the distance start display unit 16.

In the case of FIG. 5 where there is no obstruction in the tracheostomy tube A, measurement was made at almost constant values up to 4 to 5 cm, and only a change in volume in the curve shape was observed.

In the case of FIG. 6 where there is the obstruction in the tracheostomy tube A, the cross-sectional area or volume value was shown to drop around 2 cm. This site becomes the obstruction site 3.

In the case of the trachea B in FIG. 2, the cross-sectional area or volume varies depending on the patient, but narrows and expands when there is sputum. If there is no sputum, the cross-sectional area or volume graph progresses in a gradually increasing direction. This is because the trachea gradually widens downwards. If there is the obstruction in this part, the sputum must be removed with suction. In this case, since it is possible to identify the location of the sputum, a suction line with the length indicated and an external distance starting display point corresponding to the distance display start unit 36 may be used to easily remove the sputum.

In the case of the bronchus C of FIG. 2, the volume increases rapidly due to the two left and right bronchi in an area where the lungs are divided on both sides. Since it is not possible to remove the sputum from this area without a bronchus endoscope, it is sufficient to display, as a site of the bronchus C, the site where the volume increases twice.

The technical idea of the present invention described above has been specifically described in the preferred embodiments, but it should be noted that the above embodiments are for the explanation and not for the limitation. In addition, those with ordinary knowledge in the technical field of the present invention will be able to understand that various embodiments are possible within the scope of the technical idea of the present invention. Therefore, the true technical protection scope of the present invention should be determined by the technical idea of the accompanying claims.

What is claimed is:

1. A device for measuring an obstruction of a tracheostomy tube, a trachea, and a bronchus, the device comprising:

an obstruction measurement unit configured to be coupled to a tracheostomy tube entrance where a tracheostomy has been performed, and configured to transmit a sound wave and receive a reflected sound wave to measure an obstruction degree in any one of the tracheostomy tube, the trachea, or the bronchus; and a body connection unit configured to connect the obstruction measurement unit to the tracheostomy tube entrance, the body connection unit comprising a distance reference unit disposed in a sound wave route, the distance reference unit defining a preset cross-sectional area or volume to identify a starting point of an internal obstruction site of any one of the tracheostomy tube, the trachea or the bronchus.

2. The device of claim 1, wherein the obstruction measurement unit comprises at least one processor including:

a sound source generation unit configured to generate and output a sound source signal of the sound wave;

a sound wave transmission unit configured to receive the sound source signal, and generate and transmit the sound wave;

a sound wave reception unit configured to receive the reflected sound wave from an inside of any one of the tracheostomy tube, the trachea, or the bronchus; and a sound wave analysis unit configured to calculate a reflected site using transmission and reception time of the received sound wave, and then calculate an internal cross-sectional area or volume of any one of the tracheostomy tube, the trachea, or the bronchus to output the obstruction degree.

3. The device of claim 2, wherein the obstruction degree comprises an obstruction site as distance information and cross-sectional area or volume information of the obstruction site.

4. The device of claim 2, wherein the sound wave analysis unit further comprises a near field communication unit configured to transmit an obstruction alarm when the internal cross-sectional area or volume of any one of the calculated tracheostomy tube, trachea or bronchus is smaller than a preset cross-sectional area or volume.

5. The device of claim 1, the device further comprising a display unit configured to indicate an obstruction site of one of the tracheostomy tube, the trachea, or the bronchus measured in the obstruction measurement unit.

6. The device of claim 5, wherein the display unit further comprises an obstruction notification unit configured to output an obstruction alarm when a calculated internal cross-sectional area or volume of any one of the tracheostomy tube, trachea, or bronchus is smaller than a preset cross-sectional area or volume.

7. The device of claim 1, wherein the sound wave comprises at least one of an audible frequency sound wave or an ultrasonic wave.

8. A device for measuring an obstruction of a tracheostomy tube, a trachea, and a bronchus, the device comprising:

a body having an obstruction measurement unit disposed therein;

a body connection unit configured to be connected to a tracheostomy tube entrance;

a connection tube connecting the body and the body connection unit; and a display unit connected to the body and configured to output at least one of an operating status of the body, obstruction measurement information, and an obstruction alarm, wherein the obstruction measurement unit is configured to transmit a sound wave and receive a reflected sound wave to measure an obstruction degree in any one of the tracheostomy tube, the trachea, or the bronchus, and wherein the body connection unit includes a distance reference unit disposed in a sound wave route, the distance reference unit defining a preset cross-sectional area or volume to identify a starting point of an internal obstruction site of any one of the tracheostomy tube, the trachea, or the bronchus.

9. The device of claim 8, wherein the obstruction measurement unit comprises at least one processor including:

a sound source generation unit configured to generate a sound source signal of the sound wave;

a sound wave transmission unit configured to generate and transmit the sound wave using the sound source signal;

a sound wave reception unit configured to receive the reflected sound wave from an inside of one of the tracheostomy tube, the trachea, or the bronchus; and a sound wave analysis unit configured to calculate a reflected site using transmission and reception time of the received sound wave, and then calculate an internal cross-sectional area or volume of one of the tracheostomy tube, trachea, or bronchus to output an obstruction degree.

10. The device of claim 9, wherein the sound wave comprises at least one of an audible frequency sound wave or an ultrasonic wave.

11. The device of claim 8, wherein the obstruction measurement unit further comprises a near field communication unit configured to perform communication with external devices.

12. The device of claim 8, the device further comprising a replacement coupling tube that replaceably connects the body connection unit and the tracheostomy tube entrance.

13. The device of claim 12, wherein the replacement coupling tube further comprises a distance start display unit configured to provide a distance indication reference site of the display unit by having a preset cross-section or volume in a sound wave flow path inside.

* * * * *